United States Patent [19]

Horino et al.

[11] Patent Number: 5,739,100
[45] Date of Patent: Apr. 14, 1998

[54] CIS-3-HEXENAL-CIS-3-HEXENYL ACETAL COMPOUND, PROCESS FOR PREPARING SAME, AND FRAGRANCE-OR FLAVOR-IMPARTING OR FRAGRANCE-OR FLAVOR-RETAINING AGENT AND PERFUME COMPOSITION CONTAINING SAME

[75] Inventors: Hiroshi Horino, Yokohama; Shin-ichi Hirakawa, Fujisawa, both of Japan

[73] Assignee: Nippon Zeon Co., Ltd., Tokyo, Japan

[21] Appl. No.: 652,462

[22] PCT Filed: Dec. 19, 1994

[86] PCT No.: PCT/JP94/02139

§ 371 Date: Jun. 14, 1996

§ 102(e) Date: Jun. 14, 1996

[87] PCT Pub. No.: WO95/16660

PCT Pub. Date: Jun. 22, 1995

[30] Foreign Application Priority Data

Dec. 17, 1993 [JP] Japan ................... 5-343328
Feb. 28, 1994 [JP] Japan ................... 6-055317

[51] Int. Cl.[6] .................................................. A61K 7/46
[52] U.S. Cl. ...................... 512/25; 508/596; 426/650
[58] Field of Search ....................... 512/25; 568/596; 426/650

[56] References Cited

U.S. PATENT DOCUMENTS

| 3,751,486 | 8/1973 | Schleppnik et al. | 512/25 |
| 4,209,644 | 6/1980 | Ichikawa et al. | 568/596 |

FOREIGN PATENT DOCUMENTS

| 3-34952 | 2/1991 | Japan. | |
| 5-97760 | 4/1993 | Japan. | |
| 1025046 | 4/1966 | United Kingdom | 568/596 |

OTHER PUBLICATIONS

Takei et al, Chem. Abst; vol. 29, #8229–30 (1935).
"Perfume and Flavor Chemicals", S. Arctander, Steffen, Arctander's Publications, Las Vegas, NV 1969; abstract.

*Primary Examiner*—James H. Reamer
*Attorney, Agent, or Firm*—Armstrong, Westerman, Hattori, McLeLand & Naughton

[57] ABSTRACT

A compound represented by formula (1):

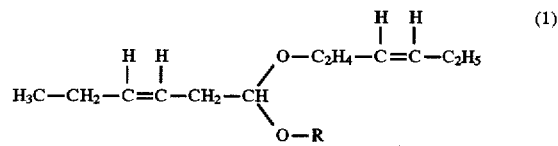

wherein R is alkyl or other hydrocarbyl, and a fragrance/flavor-imparting agent, a fragrance/flavor-retaining agent, and a perfume composition, each containing this compound as an active ingredient; and a process for preparing this compound either by reacting a compound of formula (2):

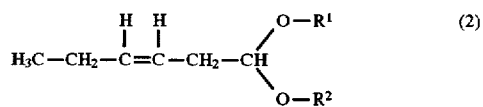

wherein $R^1$ and $R^2$ are hydrocarbyl, with cis-3-hexen-1-ol, or by reacting cis-3-hexenal-di-cis-3-hexenyl acetal with an alcohol, $R^7OH$.

31 Claims, No Drawings

CIS-3-HEXENAL-CIS-3-HEXENYL ACETAL COMPOUND, PROCESS FOR PREPARING SAME, AND FRAGRANCE-OR FLAVOR-IMPARTING OR FRAGRANCE-OR FLAVOR-RETAINING AGENT AND PERFUME COMPOSITION CONTAINING SAME

TECHNICAL FIELD

This invention relates to a cis-3-hexenal-cis-3-hexenyl acetal compound, a process for producing the same, a fragrance- or flavor-imparting or fragrance- or flavor-retaining agent containing the same, and a perfume composition containing the same.

BACKGROUND ART

Fragrance- or flavor-imparting agents and fragrance- or flavor-retaining agents are widely used in the fields including beverages and comestibles, cosmetics, sanitary and hygienic goods, detergents, bath refreshing additives, and medicines and agricultural chemicals. Fragrance- or flavor-imparting agents are used for imparting fragrance or flavor. Fragrance- or flavor-retaining agents are used for enhancing or modifying, or retaining pleasant odor of a perfume or sweet taste of a flavoring agent. Fragrance-imparting agents and flavor-imparting agents are referred to as "fragrance/flavor-imparting agents", and fragrance-retaining agents and flavor-retaining agents are referred to as "fragrance/flavor-imparting agents" in this specification.

Fragrance/flavor-imparting agents include numerous kinds of fragrance-imparting agents and flavor-imparting agents. As examples of fragrance/flavor-retaining agents, there can be mentioned solvents such as benzyl benzoate, dialkyl phthalates, Hercolyn, limonene dimer, alkylene glycols, polyalkylene glycols, alkyl citrates and dialkyl adipates; perfumes such as myrrh, Peru balsam, Tolu balsam, musks, civet, vanillin, hydroxycitronellal, olibanum, vetivert, benzyl isoeugenol, ambrette, benzoin, labdanum, clary sage, cinnamic alcohol, orris, styrax, costus, coumarin, methyl naphthyl ketone, cinnamyl cinnamate, ethyl cinnamate, 2-ethoxynaphthalene, naphthol ether, ambergris, rose phenone, oak moss, dimethyl hydroquinone, elemi, mastic indole, patchouli basil, musk ketone and diphenyl methane; and zeolite, starch, talc, plastics, clays and cellulose. A suitable fragrance/flavor-retaining agent is chosen from these fragrance/flavor-retaining agents depending upon the particular use thereof.

In recent years, green note fragrance/flavor-imparting agents including cis-3-hexenyl alcohol (leaf alcohol) are widely used, and analogues thereof such as esters are now being developed. As an example of such analogues, synthesis of cis-3-hexenal-di-cis-3-hexenyl acetal has been reported in S. Arctander, "Perfume and Flavor Chemicals", Steffen, Arctander's Publications, Las Vegas, Nev. 1969. In this publication, it is reported that this compound has a low purity and its nature is extremely unstable, and thus, the compound would be of no practical use as a fragrance/flavor-imparting agent.

The present inventors have conducted researches into compounds of the type described in the above publication, and found that, when the compounds are highly purified, the compounds exhibit pleasant and strong fragrance and flavor, and are stable to a sufficient extent for the use as a fragrance/flavor-imparting agent.

DISCLOSURE OF INVENTION

An object of the present invention is to provide a novel cis-3-hexenal-cis-3-hexenyl acetal compound having favorable characteristics as a fragrance/flavor-imparting agent and/or a fragrance/flavor-retaining agent.

Another object of the present invention is to provide a process for industrially advantageously producing the novel cis-3-hexenal-cis-3-hexenyl acetal compound.

Still another object of the present invention is to provide a fragrance/flavor-imparting or fragrance/flavor-retaining agent comprising as an active ingredient a cis-3-hexenal-cis-3-hexenyl acetal compound.

In one aspect of the present invention, there is provided a cis-3-hexenal-cis-3-hexenyl acetal compound represented by the following formula (1):

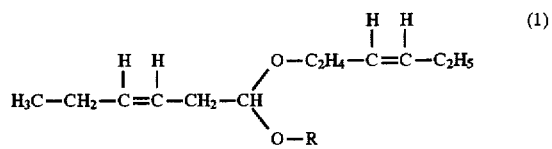

wherein R represents an alkyl group having 1 to 20 carbon atoms, which may have a substituent.

In another aspect of the present invention, there is provided a process for preparing a cis-3-hexenal-cis-3-hexenyl acetal compound represented by the following formula (3):

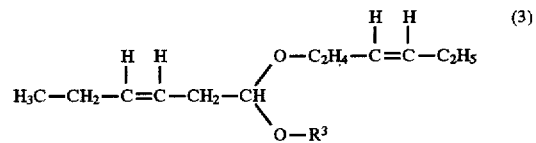

wherein $R^3$ represents a hydrocarbon group which may have a substituent, which comprises conducting an acetal exchange reaction in the presence of an acid catalyst between an acetal compound represented by the following formula (2):

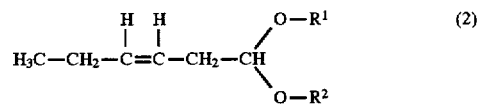

wherein $R^1$ and $R^2$ independently represent a hydrocarbon group except for a 3-hexenyl group, which may have a substituent, and cis-3-hexen-1-ol.

In still another aspect of the present invention, there is provided a process for preparing a cis-3-hexenal-cis-3-hexenyl acetal compound represented by the following formula (6):

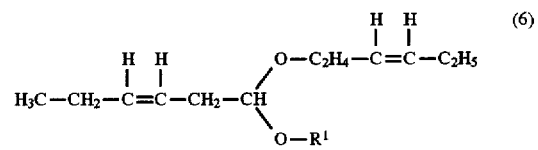

wherein $R^1$ is a hydrocarbon group, except for 3-hexenyl group, which may have a substituent, which comprises conducting an acetal exchanging reaction in the presence of an acid catalyst between cis-3-hexenal-di-cis-hexenyl acetal represented by the following formula (4):

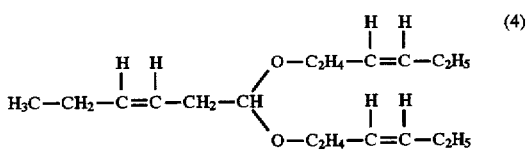

and an alcohol represented by the following formula (5):

$R^1OH$ (5)

wherein $R^1$ is the same as defined above for formula (6).

In a further aspect of the present invention, there is provided a fragrance- or flavor-imparting or fragrance- or flavor-retaining agent comprising as an active ingredient a cis-3-hexenal-cis-3-hexenyl acetal compound represented by the above formula (3).

In a further aspect of the present invention, there is provided a perfume composition comprising as an active ingredient a cis-3-hexenal-cis-3-hexenyl acetal compound represented by the above formula (3).

BEST MODE FOR CARRYING OUT THE INVENTION

The cis-3-hexenal-cis-3-hexenyl acetal compound of formula (1) is not described in any publication and is a novel compound.

The cis-3-hexenal-cis-3-hexenyl acetal compound of formula (6) also is a novel compound.

In the novel acetal compound of formula (1), R in the formula is an alkyl group having 1 to 20 carbon atoms which may have a substituent.

As specific examples of the alkyl group R, there can be mentioned straight chain alkyl groups such as methyl, ethyl, n-propyl, n-butyl, n-pentyl, n-hexyl, n-heptyl, n-octyl, n-nonyl, n-decyl, n-undecyl, n-dodecyl, n-tetradecyl, n-pentadecyl, n-hexadecyl, n-octadecyl and n-eicosyl, and branched alkyl groups such as isopropyl, isobutyl, sec-butyl, t-butyl, isopentyl, 2-methylbutyl, 1-methylbutyl, isohexyl, 3-methylpentyl, 2-methylpentyl, 1-methylpentyl, isoheptyl, isooctyl and 2-ethylhexyl. These alkyl groups may have a substituent, which does not exert baneful influence upon the synthesis reaction (acetal exchange reaction) for the compound of formula (1), such as an alkoxy group and a halogen group. Of these alkyl groups, an alkyl group having 1 to 10 carbon atoms and having 1 to 6 carbon atoms and having no substituent is more preferable.

In the acetal compound of formula (3), $R^3$ in the formula represents a hydrocarbon group preferably having 1 to 20 carbon atoms, which may have a substituent. As specific examples of the hydrocarbon group $R^3$, there can be mentioned alkyl groups which are listed above as regards R in formula (1); alkenyl groups such as allyl, 2-butenyl, 3-butenyl, isobutenyl, 4-pentenyl, 3-pentenyl, trans-2-pentenyl, cis-2-pentenyl, 1pentenyl, 3-methyl-2-pentenyl, 5-hexenyl, 2-hexenyl, trans-3-hexenyl, cis-3-hexenyl, heptenyl, octenyl, nonenyl, decenyl, dodecenyl, tetradecenyl, octadecenyl and eicosenyl; and alkynyl groups such as 2-butynyl, 3-butynyl, 4-pentynyl, 3-pentynyl, 2-pentynyl, 5-hexynyl, 3-hexenyl, heptynyl, octynyl, decynyl, dodecynyl, octadecynyl and eicosynyl. These alkenyl groups and alkynyl groups may have a substituent, which does not exert baneful influence upon the synthesis reaction (acetal exchange reaction) for the compound of formula (3), such as an alkoxy group and a halogen group. Of these hydrocarbon groups, an alkyl group having 1 to 15 carbon atoms and having no substituent, an alkenyl group having 2 to 15 carbon atoms and having no substituent, and an alkynyl group having 2 to 15 carbon atoms and having no substituent are preferable. An alkyl group having 1 to 8 carbon atoms and having no substituent, and an alkenyl group having 2 to 8 carbon atoms and having no substituent are more preferable.

In the acetal compound of formula (6), $R^1$ in the formula represents a hydrocarbon group including those which are listed as regards $R^3$ in formula (3), except for 3-hexenyl group.

The acetal compounds represented by the formulae (1) and (3) are prepared by a process wherein the acetal compound of formula (2) and cis-3-hexen-1-ol are subjected to an acetal exchange reaction in the presence of an acid catalyst, or a process wherein the acetal compound of formula (4) and an alcohol $R^1OH$ are subjected to an acetal exchange reaction in the presence of an acid catalyst.

In the acetal compound of formula (2) and the alcohol of formula (5), which are used as starting materials, $R^1$ in these formulae is as defined above as regards $R^1$ in formula (6), and $R^2$ is a hydrocarbon group which may have a substituent, and includes alkyl, alkenyl (except for 3-hexenyl) and alkynyl groups, which are listed as regards $R^1$ in formula (6).

The acid catalyst used in the above-mentioned two acetal exchange reactions is not particularly limited and may be a conventional acid catalyst. As specific examples of the acid catalyst, there can be mentioned inorganic acids such as hydrochloric acid, phosphoric acid and nitric acid; inorganic acid salts such as ammonium chloride and ammonium nitrate; sulfonic acids such as methanesulfonic acid, p-toluenesulfonic acid and benzenesulfonic acid; sulfonic acid salts such as pyridinium p-toluenesulfonate; acid-type ion exchange resins; and polyvinyl pyridine hydrochloride. Of these sulfonic acids and their salts are preferable, and p-toluenesulfonic acid and its pyridinium salt are more preferable.

The amount of cis-3-hexen-1-ol is usually in the range of 0.1 to 20 moles, preferably 0.5 to 10 moles and more preferably 1 to 5 moles, per mole of the acetal compound of formula (2). The amount of the alcohol of formula (5) is usually in the range of 0.05 to 10 moles, preferably 0.1 to 5 moles and more preferably 1 to 2.5 moles, per mole of the acetal compound of formula (4).

The amount of the acid catalyst used for the acetal exchange reaction for the compound of formula (3) is usually in the range of 0.0001 to 0.1 mole, and preferably 0.001 to 0.1 mole, per mole of the acetal compound of formula (2). The amount of the acid catalyst used for the acetal exchange reaction for the compound of formula (6) also is in the same range per mole of the acetal compound of formula (4).

The reaction temperature and reaction time in the two acetal exchange reactions are usually 0° to 100° C., preferably 10° to 50° C., and several minutes to 10 hours, preferably 10 minutes to 5 hours, respectively. The reaction procedure employed is not particularly limited, and a procedure wherein the respective reaction ingredients are mixed and stirred is employed. In some cases, an alcohol produced is preferably distilled off in succession to enhance the rate of reaction. In some cases, the reaction is carried out under a reduced pressure which is higher than the vapor pressure of the starting acetal compound (2) or (4) and the vapor pressure of cis-3-hexen-1-ol or alcohol $R^1OH$, and is lower than the vapor pressure of the alcohol produced.

After completion of the acetal exchange reaction, the cis-3-hexenal-cis-3-hexenyl acetal compound of formula (1), (3) or (6) can be isolated. As the isolation procedure, there can be mentioned, for example, a procedure wherein the reaction liquids are washed with an aqueous alkali solution and then the organic phase is distilled. In some cases, it is preferable for preventing or minimizing decomposition occurring during the distillation that an alkali metal salt of carbonic acid such as calcium carbonate or sodium carbonate, or an amine such as triethanolamine is added.

By the above-mentioned acetal exchange processes, the intended cis-3-hexenal-cis-3-hexenyl acetal compounds of formula (1), (3) and (6) can be obtained in a high yield and with a high purity.

It is known that part of the compounds of formula (3), for example, cis-3-hexenal-di-cis-3-hexenyl acetal of formula (4), is prepared by condensing cis-3-hexenal with cis-3-hexenol in the presence of a catalyst and a dehydrating agent (S. Arctander, "perfume and Flavor Chemicals", Steffen Arctander's Publications, Las Vegas, Nev. 1969). However, salient amounts of by-products are produced and the intended compound cannot be obtained in a high yield and with a high purity.

The fragrance/flavor-imparting effect and fragrance/flavor-retaining effect of the cis-3-hexenal-cis-3-hexenyl acetal compounds vary depending upon the particular cis-3-hexenal-cis-3-hexenyl acetal compounds. In general these compounds exhibit a fresch and natural green-note, and retain deep and soft flavors. The green-note of the compounds delicately vary depending upon the particular kind of $R^3$. For example, a cis-3-hexenal-cis-3-hexenyl acetal compound wherein $R^3$ is a hexenyl group with a carbon-carbon unsaturated bond exhibits a light floral green-note, and a cis-3-hexenal-cis-3-hexenyl acetal compound wherein $R^3$ is a a saturated alkyl group such as an ethyl group exhibits a vegitable green-note. These compounds retain an aromatic flavor spanning from top-note to middle-note, and their formulations exhibit fragrance and are compatible with many perfume materials.

A cis-3-hexenal-cis-3-hexenyl acetal compound wherein $R^3$ is an ethyl group, i.e., cis-3-hexenal-ethyl-cis-3-hexenyl acetal, has a cucumber-like fresh odor, which is a fresh floral green-type fragrance with a slightly powdery tone. Thus this acetal compound enhances a refreshed natural feeling and is useful as an active ingredient of a fragrance-imparting agent. When the cis-3-hexenal-ethyl-cis-3-hexenyl acetal is incorporated, floral perfume formulations such as rose, jasmine and lily of the valley are obtained. This acetal compound imparts a fantastic feeling of high quality to perfumes for soaps, detergents and cosmetics, and enhances retention of these perfumes. When the compound is incorporated in a fruity perfume such as apple, strawberry, pineapple, banana and peach, the sweet, fresh and natural flavor of the fruity perfume is enhances, and thus, the flavor of beverages, ices and confectionary is improved.

A cis-3-hexenal-cis-3-hexenyl acetal compound wherein $R^3$ is a 3-hexenyl group, i.e., cis-3-hexenal-di-cis-3-hexenyl acetal exhibits a mild and voluminous floral green fragrance with a slightly powdery tone of mimosa-like floral perfume. Therefore this acetal compound imparts a natural green tone to various compounds and, further it enhances the retention of fragrance or flavor of the compounds.

When the cis-3-hexenal-cis-3-hexenyl acetal compound of formula (3) is used as a fragrance/flavor-imparting agent or a fragrance/flavor-retaining agent in combination with a perfume, the perfume used is not particularly limited and can be chosen from synthetic perfumes and natural perfumes. As specific examples of the natural perfumes, there can be mentioned essential oils such as orange oil, lemon oil, lime oil, petigrain oil, yuzu oil, neroli oil, bergamot oil, lavender oil, lavandin oil, abies oil, bay oil, rose wood oil, ylang-ylang oil, citronella oil, geranium oil, peppermint oil, spearmint oil, eucalyptus oil, lemongrass oil, patchouli oil, jasmine oil, rose oil, cedar wood oil, vetivert oil, galbanum oil, oak moss oil, pine oil, camphor oil, sandalwood oil, ho leaf oil, turpentine oil, clove oil, clove leaf oil, cassia oil, nutmeg oil, cananga oil and thyme oil; and animal perfumes such as musk, civet, castoreum and ambergris. As specific examples of the synthetic perfumes, there can be mentioned linalool, linalyl acetate, geraniol, citronellol, aliphatic aldehydes having 6 to 12 carbon atoms, phenylethyl alcohol, benzyl acetate, geranyl acetate, geranyl formate, vanillin, nitro musks, galaxolide, tonalid, pentalide, santalex, amyl salicylate, amyl acetate, γ-undecalactone, ethyl methylphenylglycidate and heliotropin. These perfumes may be used either alone or as a perfume composition comprising at least two perfumes.

According to the need, conventional fragrance/flavor-imparting agents and fragrance/flavor-retaining agents can be used in combination with the fragrance/flavor-imparting or fragrance/flavor-retaining agent of the present invention. Auxiliaries, diluents and other additives such as enzymes, colorants, antioxidants, preservatives, germicides can also be used. Further, nourishing and repairing agents such as crude drugs, vitamins, nutrients, and fats and fatty oils, and modifiers such as bleaching agents, deodorizers and softeners, can also be used in combination with the fragrance/flavor-imparting or fragrance/flavor-retaining agent of the present invention.

The invention will now be specifically described by the following examples.

EXAMPLE 1

Synthesis of cis-3-hexenal-ethyl-cis-3-hexenyl acetal (R=ethyl)

A reactor was charged with 34.5 g of cis-3-hexenal-diethyl acetal, 20.0 g of cis-3-hexen-1-ol and 4.0 g of pyridinium p-toluenesulfonate. The reactor was equipped with a reflux condenser, the top part of which is connected through a cold trap to a vacuuming system. The content was stirred at 50° C. for 3 hours under a reduced pressure of 10 mmHg.

After completion of the reaction, the reaction mixture was diluted with ether and the crystal precipitated was removed by filtration. The filtrate was washed with an aqueous sodium carbonate solution and then with water. To the organic phase, 1 g of triethanolamine was added and the mixture was distilled under a reduced pressure of 10 mmHg to remove low-boiling ingredients, and the remainder was distilled under a reduced pressure of 2 mmHg to give 20.5 g (yield 45%) of cis-3-hexenal-ethyl-cis-3-hexenyl acetal having a boiling point of 86°–87° C. at 2 mmHg (the yield is by mole on the basis of cis-3-hexenal-diethyl acetal).

The spectral data of cis-3-hexenal-cis-hexenyl acetal are shown below.

IR (neat, KBr, $cm^{-1}$): 3010, 2964, 2933, 2875, 2360, 1657, 1462, 1444, 1371, 1344, 1304, 1211, 1120, 1063, 1030, 903, 849, 793, 723

$^1$H-NMR (400 MHz, $CDCl_3$) δ (ppm): 0.89 (t, 6H, J=7.33 Hz), 1.12 (t, 3H, J=6.8 Hz), 1.97 (m, 4H), 2.21–2.32 (m, 4H), 3.33–3.62 (m, 4H), 4.41 (t, 1H, J=5.9 Hz), 5.27 (m, 2H), 5.39 (m, 2H)

$^{13}$C-NMR (400 MHz, $CDCl_3$) δ (ppm): 14.1, 14.2, 15.2, 20.6, 20.7, 27.9, 31.8, 61.1, 65.3, 102.6, 123.1, 124.9, 133.6, 133.9

MS (mass spectrometry) (EI, 70 eV) m/e (%): 181(5), 180(9), 157(21), 127(55), 98(17), 83(100), 75(30), 67(14), 55(100), 41(38)

EXAMPLE 2

Synthesis of cis-3-hexenal-di-cis-3-hexenyl acetal (R=cis-3-hexenyl) (1)

A reactor was charged with 43.1 g of cis-3-hexenal-diethyl acetal, 75.1 g of cis-3-hexen-1-ol and 5.0 g of pyridinium p-toluenesulfonate. The reactor was equipped with a reflux condenser, the top part of which is connected through a cold trap to a vacuuming system. The content was stirred at 40° C. for 2 hours under a reduced pressure of 10 mmHg.

After completion of the reaction, the reaction mixture was washed with an aqueous sodium carbonate solution and then with water. To the organic phase, 1.5 g of tri-ethanolamine was added and the mixture was distilled under a reduced pressure of 10 mmHg to remove the predominant part of the initial boiling ingredients, and the remainder was distilled under a reduced pressure of 1 mmHg to give of cis-3-hexenal-di-cis-3-hexenyl acetal having a boiling point of 105°–106° C. at 1 mmHg (the yield is by mole on the basis of cis-3-hexenal-diethyl acetal). Gas chromatography revealed that the purity of this compound was 99%.

EXAMPLE 3

Synthesis of cis-3-hexenal-di-cis-3-hexenyl acetal (R=cis-3-hexenyl) (2)

A reactor was charged with 17.3 of cis-3-hexenal-diethyl acetal, 40.1 g of cis-3-hexan-1-ol and 0.40 g of p-toluenesulfonic acid. The reactants were allowed to react in the same manner as in Example 2 except that the reaction time was changed to 30 minutes. Thus cis-3-hexenal-di-cis-3-hexenyl acetal having a boiling point of 125°–128° C. at 2 mmHg was obtained in a yield of 79% (the yield is by mole on the basis of cis-3-hexenal-diethyl acetal). Gas chromatography revealed that the purity of this compound was 99%.

The spectral data of cis-3-hexenal-di-cis-3-hexenyl acetal obtained in Examples 2 and 3 are shown below.

IR (neat, KBr, cm$^{-1}$): 3010, 2964, 2933, 2873, 1655, 1457, 1375, 1346, 1304, 1279, 1221, 1120, 1070, 1053, 874, 850, 791, 721

$^1$H-NMR (400 MHz, CDCl$_3$/TMS) δ (ppm): 14.0, 14.1, 20.5, 20.6, 27.8, 31.6, 65.2, 102.6, 123.1, 124.9, 133.4, 133.7

MS (EI, 70 eV) m/e (%): 181(7), 180(41), 157(6), 127 (15), 98(54), 83(78), 75(6), 67(12), 55(100), 41(55)

EXAMPLES 4–6

Synthesis of:

(1) cis-3-hexenal-methyl-cis-3-hexenyl acetal (R=methyl), (2) cis-3-hexenal-propyl-cis-3-hexenyl acetal (R=n-propyl), and (3) cis-3-hexenal-butyl-cis-3-hexenyl acetal (R=n-butyl).

A flask was charged with 98.15 g (0.35 mole) of cis-3-hexenal-di-cis-3-hexenyl acetal, 0.35 mole of methanol (Example 4), n-propanol (Example 5) or n-butanol (Example 6), and 0.74 g of p-toluenesulfonic acid monohydrate, and the content was stirred at room temperature for 1 hour by a magnetic stirrer to effect an acetal exchange reaction. The reaction mixture was washed with 50 ml of a 5% aqueous sodium carbonate solution, and the separated organic phase was subjected to fractional distillation under a reduced pressure of 2 mmHg to give the above-mentioned acetal compounds (1), (2) or (3).

The boiling point and yield of the acetal compounds (1), (2) and (3) were as follows. (the yield is by mole on the basis of the charged cis-3-hexenal-di-cis-3-hexenyl acetal)

| Example No. | Acetal compound | Boiling point (°C./mmHg) | Yield (mole %) |
|---|---|---|---|
| 4 | (1) R = methyl | 78–81/2 | 38.1 |
| 5 | (2) R = n-propyl | 100–103/2 | 38.9 |
| 6 | (3) R = n-butyl | 113–117/2 | 41.0 |

The spectral data of the acetal compounds (1), (2) and (3) are shown below.

(1) Cis-3-hexenal-methyl-cis-3-hexenyl acetal

IR (neat, KBr, cm$^{-1}$): 3010, 2964, 2933, 2875, 2829, 1655, 1464, 1405, 1375, 1360, 1348, 1306, 1281, 1225, 1190, 1120, 1068, 968, 918, 870, 847, 827, 793, 723

$^1$H-NMR (400 MHz), CDCl$_3$/TMS) δ (ppm): 0.97(6H), 2.06 (4H), 2.30–2.40 (m, 4H), 3.33 (s, 3H), 3.41–3.48 (m, H), 3.55–3.62 (m, H), 4.41 (t, 1H, J=5.62 Hz), 5.31–5.39 (m, 2H), 5.44–5.53 (m, 2H)

$^{13}$C-NMR (400 MHz), CDCl$_3$/TMS) δ (ppm): 14.1, 14.2, 20.7, 20.8, 28.0, 31.4, 52.8, 65.6, 103.6, 123.0, 125.0, 133.7, 134.1

MS (EI, 70 eV) m/e (%): 212 (M$^+$, 0.05), 181(1.5), 180(1), 143(11), 113(31), 97(2), 83(100), 81(13), 71(12), 61(8), 55(62), 45(5), 41(22)

(2) Cis-3-hexenal-propyl-cis-3-hexenyl acetal

IR (neat, KBr, cm$^{-1}$): 3010, 2964, 2935, 2875, 1655, 1464, 1404, 1375, 1350, 1304, 1281, 1219, 1120, 1068, 1036, 993, 970, 908, 874, 793, 725

$^1$H-NMR (400 MHz, CDCl$_3$/TMS), δ (ppm): 0.91–0.99 (m, 9H), 1.59 (m, 2H), 2.06 (m, 4H), 2.29–2.41 (m, 4H), 3.37–3.48 (m, 2H), 3.52–3.62 (m, 2H), 4.49 (t, 1H, J=5.86 Hz), 5.32–5.39 (m, 2H), 5.43–5.52 (m, 2H)

$^{13}$C-NMR (400 MHz, CDCl$_3$/TMS) δ (ppm): 10.8, 14.2, 14.3, 20.7, 20.8, 23.1, 28.0, 31.9, 65.3, 67.5, 102.8, 123.3, 125.0, 133.6, 133.9

MS (EI, 70 eV) m/e (%): 240 (M$^+$, 0.1), 181(3), 180(1), 171(11), 141(28), 99(5), 89(17), 83(100), 81(19), 67(8), 55(58), 43(21), 41(23)

(3) Cis-3-hexenal-butyl-cis-3-hexenyl acetal

IR (neat, KBr, cm$^{-1}$): 3010, 2962, 2933, 2873, 1655, 1464, 1435, 1404, 1379, 1346, 1306, 1279, 1217, 1119, 1070, 1045, 970, 891, 872, 849, 795, 725

$^1$H-NMR (400 MHz), CDCl$_3$/TMS), δ (ppm): 0.90–0.99 (m, 9H), 1.33–1.44 (m, 2H), 1.51–1.60 (m, 2H), 2.02–2.10 (m, 4H), 2.29–2.40 (m, 4H), 3.40–3.48 (m, 2H), 3.55–3.62 (m, 2H), 4.48 (t, 1H, J=5.86 Hz), 5.32–5.39 (m, 2H), 5.33–5.52 (m, 2H)

$^{13}$C-NMR (400 MHz, CDCl$_3$/TMS) δ (ppm): 13.9, 14.2, 14.3, 19.5, 20.7, 20.8, 28.0, 31.8, 32.0, 65.3, 65.6, 102.8, 123.3, 125.0, 133.6, 133.9

MS (EI, 70 eV) m/e (%): 254 (M$^+$, 0.16), 185(11), 181(3), 180(2), 155(25), 137(2), 103(14), 83(100), 81(19), 67(8), 57(27), 55(57), 41(24)

EXAMPLE 7

Perfume composition (1) containing cis-3-hexenal-ethyl-cis-3-hexenyl acetal

The ingredients shown in Table 1 were mixed together to prepare a rosa damascena (rose damask)-tone floral base fragrant composition. To 100 parts by weight of this rosa damascena (rose damask)-tone floral base fragrant composition, 1 part by weight of cis-3-hexenal-ethyl-cis-3-hexenyl acetal was incorporated to prepare a perfume composition. The top note was of freshness with a natural green tone, and was of broad diffusibility and good retainability. The natural tone of the perfume was enhanced.

TABLE 1

| Ingredient | Amount (parts by weight) |
| --- | --- |
| Citral | 0.5 |
| C9 aldehyde | 0.5 |
| Damascenone | 1.0 |
| Rose oxide | 5.0 |
| Phenylethyl acetate | 5.0 |
| Geranyl acetate | 8.0 |
| Terpineol | 10.0 |
| Farnesol | 10.0 |
| Phenylethyl alcohol | 15.0 |
| Geranium oil | 30.0 |
| Nerol | 90.0 |
| Geraniol | 160.0 |
| Citronellol | 320.0 |
| Carryophyllene | 5.0 |
| Eugenol | 6.0 |
| Sandalwood oil | 10.0 |
| Methyl eugenol | 24.0 |
| 2-Phenoxyethanol | 300.0 |
| Total | 1000.0 |

EXAMPLE 8

Perfume composition (2) containing cis-3-hexenal-ethyl-cis-3-hexenyl acetal (R=ethyl)

The ingredients shown in Table 2 were mixed together to prepare a white peach fruit fragrant composition. To 100 parts by weight of this white peach fruit fragrant composition, 0.65 part by weight of cis-3-hexenal-ethyl-cis-3-hexenyl acetal was incorporated to prepare a perfume composition. The perfume exhibited natural tone flavor with an enhanced fresh sweet taste of white peach.

TABLE 2

| Ingredient | Amount (parts by weight) |
| --- | --- |
| Hexyl acetate | 0.9 |
| Benzaldehyde | 1.2 |
| Benzyl alcohol | 1.2 |
| Cis-3-hexenyl acetate | 4.0 |
| Cis-3-hexenol | 5.0 |
| Hexanol | 15.0 |
| Trans-2-hexenyl acetate | 15.0 |
| Rinalool | 18.0 |
| γ-Tridecalactone | 0.5 |
| γ-Nonalactone | 0.5 |
| γ-Heptalactone | 1.0 |
| δ-Octalactone | 1.2 |
| γ-Octalactone | 5.0 |
| Jasmine lactone | 5.0 |
| γ-Dodecalactone | 14.0 |
| δ-Decalactone | 22.0 |
| γ-Hexalactone | 27.0 |
| γ-Decalactone | 85.0 |
| Triacetin | 778.5 |
| Total | 1000.0 |

EXAMPLE 9

Perfume compositions (3) and (4) containing cis-3-hexenal-di-cis-3-hexenyl acetal (R=hexenyl)

The ingredients shown in Table 3 were mixed together to prepare two kinds of fruity sweet green base perfume compositions (A) and (B). The composition (B) contained cis-3-hexenal-di-cis-3-hexenyl acetal, but the composition (A) did not contain the acetal compound.

The ingredients shown in Table 4 were mixed together to prepare two kinds of fresh spicy green base perfume compositions (A) and (B). The composition (B) contained the acetal compound, but the composition (A) did not contain the acetal compound.

The compositions (B) containing the acetal compound exhibited milder and more natural fragrances than those of the compositions (A).

TABLE 3

Fruity Green Base

| Ingredient | Composition A (weight parts) | Composition B (weight parts) |
| --- | --- | --- |
| Citral | 0.2 | 0.2 |
| Cis-3-hexenyl anthranilate | 0.3 | 0.3 |
| Hexyl n-butyrate | 0.4 | 0.4 |
| Cis-3-hexenyl n-butyrate | 0.5 | 0.5 |
| Raspberry ketone (1%) | 0.6 | 0.6 |
| Zeppin (methyl jasmonate) | 0.8 | 0.8 |
| γ-Decalactone | 1.0 | 1.0 |
| Extra green (cis-3-hexenol) | 1.2 | 1.2 |
| Methyl benzoate | 2.0 | 2.0 |
| γ-Nonalactone | 3.0 | 3.0 |
| Cepionate (methyl dihydrojasmonate) | 6.0 | 6.0 |
| Cis-3-hexyl benzoate | 6.0 | 6.0 |
| Cis-3-hexenal-di-cis-3-hexenyl acetal | — | 6.0 |
| Benzyl acetate | 6.0 | 6.0 |
| Benzyl benzoate | 8.0 | 8.0 |
| Linalool | 14.0 | 14.0 |
| γ-Undecalactone | 24.0 | 24.0 |
| Ethyl maltol (1%) | 2.0 | 2.0 |
| Vanillin (10%) | 4.0 | 4.0 |
| Triacetin | 20.0 | 20.0 |
| Total | 100.0 | 100.0 |

TABLE 4

Fresh Spicy Green Base

| Ingredient | Composition A (weight parts) | Composition B (weight parts) |
| --- | --- | --- |
| Verbena oil | 2.0 | 2.0 |
| C10-aldehyde | 3.0 | 3.0 |
| Herional | 3.0 | 3.0 |
| Basil oil | 3.0 | 3.0 |
| Lemon oil | 4.0 | 4.0 |
| Taragon oil | 5.0 | 5.0 |
| Grape fruit oil | 10.0 | 10.0 |
| Cis-3-hexenal-di-cis-3-hexenyl acetal | — | 10.0 |
| Styralyl acetate | 15.0 | 15.0 |
| Lavender oil | 20.0 | 20.0 |
| Bergamot oil (non-photosensitive non-toxic) | 25.0 | 25.0 |
| 2-Phenoxyethanol | 10.0 | — |
| Total | 100.0 | 100.0 |

EXAMPLE 10

Perfume compositions (5) and (6) containing cis-3-hexenal-di-cis-3-hexenyl acetal (R=3hexenyl)

The ingredients shown in Table 5 were mixed together to prepare two kinds of blue hyacinth base perfume compositions (A) and (B). The composition (B) contained cis-3-hexenal-di-cis-3-hexenyl acetal, but the composition (A) did not contain the acetal compound.

The ingredients shown in Table 6 were mixed together to prepare two kinds of mimosa base perfume compositions (A) and (B). The composition (B) contained the acetal compound, but the composition (A) did not contain the acetal compound.

The compositions (B) containing the acetal compound exhibited softer and more voluminous and delightful floral fragrances than those of the compositions (A).

TABLE 5

Blue Hyacinth Base

| Ingredient | Composition A (weight parts) | Composition B (weight parts) |
| --- | --- | --- |
| Sweet birch oil | 0.1 | 0.1 |
| 3-Phenylpropyl acetate | 0.1 | 0.1 |
| Cinnamyl nitrate | 0.2 | 0.2 |
| Cis-3-hexyl anthranilate | 0.3 | 0.3 |
| Cinnamyl benzoate | 0.4 | 0.4 |
| Ylang ylang absolute | 1.0 | 1.0 |
| Cinnamyl acetate | 1.4 | 1.4 |
| Cis-3-hexenal-di-cis-3-hexenyl acetal | — | 1.5 |
| 3-Phenylpropanol | 1.5 | 1.5 |
| Phenylethyl alcohol | 2.0 | 2.0 |
| Methyl eugenol | 2.0 | 2.0 |
| Phenylethyl benzoate | 3.0 | 3.0 |
| Benzyl alcohol | 3.0 | 3.0 |
| 2-Phenoxyethanol | 6.0 | 4.5 |
| 3-Methoxyphenylethanol | 10.0 | 10.0 |
| Benzyl acetate | 15.0 | 15.0 |
| Benzyl benzoate | 20.0 | 20.0 |
| Cinnamyl alcohol | 30.0 | 30.0 |
| Methyl palmitate | 2.0 | 2.0 |
| Methyl anisate | 2.0 | 2.0 |
| Total | 100.0 | 100.0 |

TABLE 6

Mimosa Base

| Ingredient | Composition A (weight parts) | Composition B (weight parts) |
| --- | --- | --- |
| Cis-3-hexyl acetate | 0.1 | 0.1 |
| p-Methylacetophenone | 0.2 | 0.2 |
| Cis-3-hexenyl benzoate | 0.3 | 0.3 |
| C9-aldehyde | 0.5 | 0.5 |
| C10-aldehyde | 0.5 | 0.5 |
| Bergamot oil | 0.6 | 0.6 |
| Cinnamyl alcohol | 0.6 | 0.6 |
| Cis-3-hexenal-di-cis-3-hexenyl acetal | — | 1.0 |
| Anisaldehyde | 1.0 | 1.0 |
| Methyl isoeugenol | 1.0 | 1.0 |
| Ylang ylang absolute | 1.0 | 1.0 |
| Ethyl benzoate | 1.5 | 1.5 |
| Benzyl alcohol | 2.0 | 2.0 |
| Helional | 3.0 | 3.0 |
| Terpineol | 3.0 | 3.0 |
| Cepionate (methyl dihydrojasmonate) | 4.0 | 4.0 |
| Benzyl benzoate | 6.0 | 6.0 |
| Lyral | 12.0 | 12.0 |
| Benzyl salycylate | 28.0 | 28.0 |
| Eugenol | 0.5 | 0.5 |
| Guaiac oil | 1.0 | 1.0 |
| Ionone-alpha | 1.0 | 1.0 |
| Ethyl linolate | 27.0 | 26.0 |
| Heliotropin | 1.2 | 1.2 |

TABLE 6-continued

Mimosa Base

| Ingredient | Composition A (weight parts) | Composition B (weight parts) |
| --- | --- | --- |
| Methyl anisate | 3.0 | 3.0 |
| Total | 100.0 | 100.0 |

EXAMPLE 11

Perfume compositions (7) and (8) containing cis-3-hexenal-di-cis-3-hexenyl acetal (R=3-hexenyl)

Floral base compositions other than green floral bases were prepared. Namely, the ingredients shown in Table 7 were mixed together to prepare two kinds of rose de mai (rose of May) base perfume compositions (A) and (B). The composition (B) contained cis-3-hexenal-di-cis-3-hexenyl acetal, but the composition (A) did not contain the acetal compound. The ingredients shown in Table 8 were mixed together to prepare two kinds of purple lilac base perfume compositions (A) and (B). The composition (B) contained the acetal compound, but the composition (A) did not contain the acetal compound. The top note of the compositions (B) containing the acetal compound was of soft, fresh and elegant floral tone.

TABLE 7

Rose-De-Mai Base

| Ingredient | Composition A (weight parts) | Composition B (weight parts) |
| --- | --- | --- |
| Rose oxide L | 0.2 | 0.2 |
| Phenylacetoaldehyde | 0.2 | 0.2 |
| Citral | 0.3 | 0.3 |
| Damascenone | 0.4 | 0.4 |
| Cis-3-hexenal-di-cis-3-hexenyl acetal | — | 0.5 |
| Rhodinyl acetate | 0.6 | 0.6 |
| Terpenol alpha | 0.8 | 0.8 |
| Benzyl alcohol | 1.0 | 1.0 |
| Nerol | 2.0 | 2.0 |
| Phenylethyl acetate | 3.0 | 3.0 |
| Rhodinol | 15.0 | 15.0 |
| Phenylethyl alcohol | 70.0 | 70.0 |
| Guail acetate | 1.0 | 1.0 |
| Clove oil | 1.0 | 1.0 |
| Methyleugenol | 2.0 | 2.0 |
| 2-Phenoxyethanol | 2.5 | 2.0 |
| Total | 100.0 | 100.0 |

TABLE 8

Purple Lilac

| Ingredient | Composition A (weight parts) | Composition B (weight parts) |
| --- | --- | --- |
| Cis-3-hexenyl anthranilate | 0.1 | 0.1 |
| Cis-3-hexenyl acetate | 0.1 | 0.1 |
| Extra green (cis-3-hexenol) | 0.3 | 0.3 |
| Zeppin (methyl jasmonate) | 0.3 | 0.3 |
| Tetrahydrogeraniol | 0.5 | 0.5 |
| Cinnamic acetate | 0.5 | 0.5 |
| Cis-3-hexenal-di-cis-3-hexenyl acetal | — | 1.0 |

TABLE 8-continued

Purple Lilac

| Ingredient | Composition A (weight parts) | Composition B (weight parts) |
| --- | --- | --- |
| Linalool | 1.0 | 1.0 |
| Ylang ylang absolute | 1.0 | 1.0 |
| Phenylacetoaldehyde glycerin acetal | 2.0 | 2.0 |
| 3-Phenylpropanol | 2.0 | 2.0 |
| Styrax resinoid | 3.0 | 3.0 |
| Anisaldehyde | 3.0 | 3.0 |
| Phenylethyldimethylcarbinol | 4.0 | 4.0 |
| Cinnamyl alcohol | 4.0 | 4.0 |
| Terpineol alpha | 6.0 | 6.0 |
| 2-Phenoxyethanol | 10.0 | 9.0 |
| Benzyl alcohol | 10.0 | 10.0 |
| Phenylethyl alcohol | 20.0 | 20.0 |
| Lilial | 30.0 | 30.0 |
| Indole | 0.2 | 0.2 |
| Dimethylhydroquinone | 2.0 | 2.0 |
| Total | 100.0 | 100.0 |

Industrial Applicability

The cis-3-hexenal-cis-3-hexenyl acetal compounds represented by the above-mentioned formulae (1), (2) and (3) are useful as a fragrance/flavor-imparting agent and a fragrance/flavor-retaining agent, and can be incorporated in the following products.

Food and drink, for example, beverages such as fruit juices, fruit wines, dairy beverages and carbonated beverages; ices such as ice creams, sherbets and ice-candies; confectionery such as Japanese and western sweets and cakes; luxuries such as jams, chewing gums, bread, coffee, cocoa chocolate, black tea and Japanese tea; soup such as soup and Japanese soup; flavorings, instant food and drink, snacks; cosmetics such as perfumes, Eau de Cologne, lotions, shampoos, hair cosmetic bases for hair cream and pomade, cosmetic bases; hygienic detergents such as washing detergents, sterilizing detergents, deodorizing detergents, and room aromatics; medical and hygienic supplies such as toothpastes, tissues and toilet paper; medicines and medical supplies such as tablets, granules, ointments, powders and others.

We claim:

1. A cis-3-hexenal-cis-3-hexenyl acetal compound represented by the following formula (1):

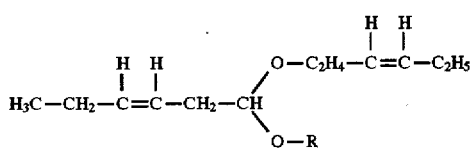

wherein R represents an alkyl group, having 1 to 20 carbon atoms.

2. The acetal compound as claimed in claim 1, wherein R is an alkyl group having 1 to 10 carbon atoms and having no substituent.

3. The acetal compound as claimed in claim 1, wherein R is an alkyl group selected from methyl, ethyl, propyl and butyl groups.

4. A process for preparing a cis-3-hexenal-cis-3-hexenyl acetal compound represented by the following formula (3): wherein $R^3$ represents a hydrocarbon group, which comprises conducting an acetal exchange reaction at a temperature of 0° to 100° C. in the presence of an acid catalyst between an acetal compound represented by the following formula (2):

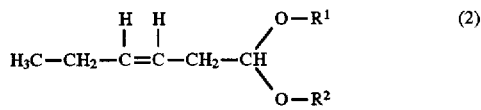

wherein $R^1$ and $R^2$ independently represent a hydrocarbon group except for a 3-hexenyl group, and 0.1 to 20 moles, per mole of acetal compound of formula (2), of cis-3-hexen-1-ol.

5. The process as claimed in claim 4, wherein $R^1$ and $R^2$ are independently selected from an alkyl group having 1 to 20 carbon atoms, an alkenyl group having 2 to 20 carbon atoms, except for 3-hexenyl group, and an alkynyl group having 2 to 20 carbon atoms.

6. The process as claimed in claim 4, wherein $R^1$ and $R^2$ are independently selected from an alkyl group having 1 to 15 carbon atoms and having no substituent, an alkenyl group having 2 to 15 carbon atoms, except for 3-hexenyl group, and having no substituent, and an alkynyl group having 2 to 15 carbon atoms and having no substituent.

7. The process as claimed in claim 4, wherein $R^1$ and $R^2$ are independently selected from an alkyl group having 1 to 8 carbon atoms and having no substituent, an alkenyl group having 2 to 8 carbon atoms and having no substituent, except for 3-hexenyl group, and an alkynyl group having 2 to 8 carbon atoms and having no substituent.

8. The process as claimed in claim 4, wherein $R^1$ and $R^2$ are independently selected from methyl, ethyl, propyl and butyl groups.

9. The process as claimed in claim 4 wherein $R^3$ is selected from an alkyl group having 1 to 20 carbon atoms, an alkenyl group having 2 to 20 carbon atoms, and an alkynyl group having 2 to 20 carbon atoms.

10. The process as claimed in claim 4 wherein $R^3$ is selected from an alkyl group having 1 to 15 carbon atoms and having no substituent, an alkenyl group having 2 to 15 carbon atoms and having no substituent, and an alkynyl group having 2 to 15 carbon atoms and having no substituent.

11. The process as claimed in claim 4 wherein $R^3$ is selected from an alkyl group having 1 to 8 carbon atoms and having no substituent, an alkenyl group having 2 to 8 carbon atoms and having no substituent, and an alkynyl group having 2 to 8 carbon atoms and having no substituent.

12. The process as claimed in claim 4 wherein $R^3$ is an alkyl group selected from methyl, ethyl, propyl and butyl groups, or a 3-hexenyl group.

13. The process as claimed in claim 4 wherein the acid catalyst is p-toluenesulfonic acid or a salt thereof.

14. The process as claimed in claim 4 wherein the amount of cis-3-hexen-1-ol is in the range of 0.5 to 10 moles per mole of the acetal compound of formula (2).

15. A process for preparing a cis-3-hexenal-cis-3-hexenyl acetal compound represented by the following formula (6):

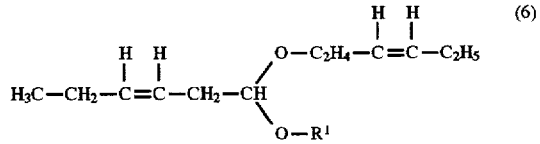

wherein $R^1$ is a hydrocarbon group, except for 3-hexenyl group, which comprises conducting an acetal exchange reaction at a temperature of 0° to 100° C. in the presence of an acid catalyst between cis-3-hexenal-di-cis-3-hexenyl acetal represented by the following formula (4):

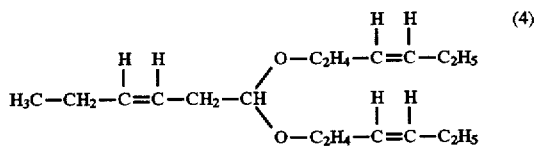

and 0.05 to 10 moles, per mole of the acetal compound of formula (4), of an alcohol represented by the following formula (5):

wherein $R^1$ is the same as defined above for formula (6).

16. The process as claimed in claim 15, wherein $R^1$ is selected from an alkyl group having 1 to 20 carbon atoms, an alkenyl group having 2 to 20 carbon atoms, except for 3-hexenyl group, and an alkynyl group having 2 to 20 carbon atoms.

17. The process as claimed in claim 15, wherein $R^1$ is selected from an alkyl group having 1 to 15 carbon atoms and having no substituent, an alkenyl group having 2 to 15 carbon atoms, except for 3-hexenyl group, and having no substituent, and an alkynyl group having 2 to 15 carbon atoms.

18. The process as claimed in claim 15, wherein $R^1$ is selected from an alkyl group having 1 to 8 carbon atoms and having no substituent, an alkenyl group having 2 to 8 carbon atoms, except for 3-hexenyl group, and having no substituent, and an alkynyl group having 2 to 8 carbon atoms.

19. The process as claimed in claim 15, wherein $R^1$ is selected from methyl, ethyl, propyl and butyl groups.

20. The process as claimed in any of claims 15 to 19, wherein the acid catalyst is p-toluenesulfonic acid or a salt thereof.

21. The process as claimed in claim 15 wherein the amount of alcohol of formula (5) is in the range of 0.1 to 5 moles per mole of the acetal compound of formula (4).

22. A fragrance- or flavor-imparting or fragrance- or flavor-retaining agent comprising as an active ingredient a cis-3-hexenal-cis-3-hexenyl acetal compound represented by the following formula (3):

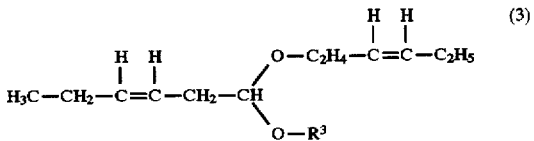

wherein $R^3$ represents a hydrocarbon group.

23. The fragrance- or flavor-imparting or fragrance- or flavor-retaining agent as claimed in claim 22, wherein $R^3$ is selected from an alkyl group having 1 to 20 carbon atoms, an alkenyl group having 2 to 20 carbon atoms, and an alkynyl group having 2 to 20 carbon atoms.

24. The fragrance- or flavor-imparting or fragrance- or flavor-retaining agent as claimed in claim 22, wherein $R^3$ is selected from an alkyl group having 1 to 15 carbon atoms and having no substituent, an alkenyl group having 2 to 15 carbon atoms and having no substituent, and an alkynyl group having 2 to 15 carbon atoms and having no substituent.

25. The fragrance- or flavor-imparting or fragrance- or flavor-retaining agent as claimed in claim 22, wherein $R^3$ is selected from an alkyl group having 1 to 8 carbon atoms and having no substituent, an alkenyl group having 2 to 8 carbon atoms and having no substituent, and an alkynyl group having 2 to 8 carbon atoms and having no substituent.

26. The fragrance- or flavor-imparting or fragrance- or flavor-retaining agent as claimed in claim 22, wherein $R^3$ is an alkyl group selected from methyl, ethyl, propyl and butyl groups, or a 3-hexenyl group.

27. A perfume composition comprising as an active perfuming ingredient or perfume-retaining ingredient a cis-3-hexenal-cis-3-hexenyl acetal compound represented by the following formula (3):

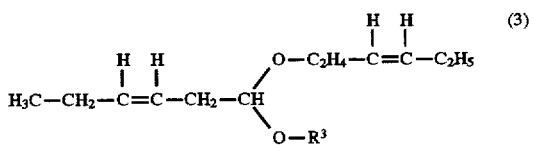

wherein $R^3$ represents a hydrocarbon group.

28. The perfume composition as claimed in claim 27, wherein $R^3$ is selected from an alkyl group having 1 to 20 carbon atoms, an alkenyl group having 2 to 20 carbon atoms, and an alkynyl group having 2 to 20 carbon atoms.

29. The perfume composition as claimed in claim 27, wherein $R^3$ is selected from an alkyl group having 1 to 15 carbon atoms and having no substituent, an alkenyl group having 2 to 15 carbon atoms and having no substituent, and an alkynyl group having 2 to 15 carbon atoms and having no substituent.

30. The perfume composition as claimed in claim 27, wherein $R^3$ is selected from an alkyl group having 1 to 8 carbon atoms and having no substituent, an alkenyl group having 2 to 8 carbon atoms and having no substituent, and an alkynyl group having 2 to 8 carbon atoms and having no substituent.

31. The perfume composition as claimed in claim 27, wherein $R^3$ is an alkyl group selected from methyl, ethyl, propyl and butyl groups, or a 3-hexenyl group.

* * * * *